(12) United States Patent
Tuck et al.

(10) Patent No.: US 7,355,083 B2
(45) Date of Patent: Apr. 8, 2008

(54) PROCESS

(75) Inventors: Michael William Marshall Tuck, London (GB); Simon Nicholas Tilley, London (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 11/668,884

(22) Filed: Jan. 30, 2007

(65) Prior Publication Data

US 2007/0149830 A1  Jun. 28, 2007

Related U.S. Application Data

(63) Continuation of application No. PCT/GB2006/050181, filed on Jun. 30, 2006.

(30) Foreign Application Priority Data

Jul. 15, 2005 (GB) .................. 0514593.3

(51) Int. Cl.
C07C 29/60 (2006.01)
C07C 29/132 (2006.01)

(52) U.S. Cl. ..................................... 568/861

(58) Field of Classification Search .................. 568/861
See application file for complete search history.

(56) References Cited

U.S. PATENT DOCUMENTS 4,642,394 A 2/1987 Che
5,214,219 A 5/1993 Casale et al.
5,276,181 A 1/1994 Casale et al.
5,354,914 A 10/1994 Gubitosa et al.
5,426,249 A 6/1995 Haas et al.
5,616,817 A 4/1997 Schuster et al.
6,002,054 A 12/1999 Ueoka et al.
6,291,725 B1 9/2001 Chopade et al.
6,841,085 B2 1/2005 Werpy et al.

FOREIGN PATENT DOCUMENTS

DE 524101 5/1931
DE 4302464 8/1994
EP 072629 2/1983
EP 0510238 A1 10/1992
EP 1000003 B1 5/2000
EP 1292556 B1 3/2003
WO 2005/095536 A2 10/2005

OTHER PUBLICATIONS

Chaminade, et al., "Glycerol hydrogenolysis on heterogenous catalysts," Green Chem., 2004, p. 359-361, vol. 6.
Dasari, et al., Applied Catalysis, 2005, p. 225-231, vol. 281.
International Search Report and Written Opinion from PCT/GB2006/050181, dated Oct. 24, 2006.

*Primary Examiner*—Elvis O. Price
(74) *Attorney, Agent, or Firm*—Senniger Powers

(57) ABSTRACT

A process for hydrogenation of glycerol in which a feed comprising glycerol is contacted with a stream of a hydrogen-containing gas and subjected to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 secs.

16 Claims, No Drawings

PROCESS

CROSS-REFERENCE TO RELATED APPLICATIONS

This application is a continuation under 35 U.S.C. §365 (c) of International (PCT) Application Serial No. PCT/GB2006/050181, filed Jun. 30, 2006, which claims priority from GB 0514593.3, filed Jul. 15, 2005, both of which are herein incorporated by reference in their entirety.

The present invention relates to a process for the hydrogenation of 1,2,3-propanetriol, also known as glycerol, in the vapour phase. More particularly it relates to the selective hydrogenation of glycerol in the vapour phase whereby alteration of the process conditions enables selection of 1,2-propanediol or propanols as the major product.

Glycerol is available in large quantities and it is anticipated that the supply of glycerol will increase as it is a by-product of processes which are becoming increasingly attractive since they are based on natural products such as oils and fats as starting materials. Examples of oils and fats include palm oil, rape seed oil, beef tallow and the like.

However, whilst glycerol is available in large quantities its present uses are limited in volume. It is therefore desirable to provide processes which enable the glycerol to be converted to useful materials. It will therefore be understood coupling downstream processes which use glycerol as a feedstock to processes which have glycerol as a by-product offers economic advantages. Thus processes to which a glycerol reactor could be coupled include bio-diesel units and fat splitters such as feed units to natural detergent plants and the like.

Although glycerol does not have uses to match its availability, it can be converted to 1,2-propanediol and 2-propanol which are valuable starting materials which have various applications. Various processes have been proposed for effecting the conversion.

In U.S. Pat. No. 5,426,249, which is incorporated herein by reference, there is described a process in which a gaseous stream of glycerol is dehydrated to acrolein. The acrolein is then condensed and hydrated to 3-hydroxypropionaldehyde which is then subjected to hydrogenation in the liquid phase. This multi-step process enables 1,2- and 1,3-propanediol to be obtained simultaneously.

U.S. Pat. No. 5,214,219, which is incorporated herein by reference, describes a process in which glycerol is converted to 1,2-propanediol and 1,2-ethanediol. In this process hydrogenation of the glycerol is carried out in the liquid phase in the presence of a copper/zinc catalyst and at a temperature of about 220° C.

An alternative processes for the liquid phase hydrogenation of glycerol is described in U.S. Pat. No. 5,616,817, which is incorporated herein by reference. The process, which is directed to the production of 1,2-propanediol, requires the glycerol to have a water content of no more than 20% by weight. The hydrogenation is carried out in the presence of a catalyst comprising cobalt, copper, manganese and molybdenum.

Chaminand et al. Green Chem. 6, (2004) 359-361 describes a process in which the glycerol is hydrogenated in the liquid phase using a supported metal catalyst. At the process conditions of 180° C. and 85 bar the reaction rate is slow with only 20% conversion being achieved after 168 hours.

An alternative process is described in Desari et al., Applied Catalysis A281, (2005) 225-231 in which a copper/chrome catalyst is used for the liquid phase hydrogenation of glycerol. However, conversion was low with conversion rates of less than 30% being noted. It is suggested that this is due to the catalyst becoming deactivated and reactivation of the catalyst between tests was required.

DE4302464 and DE524101 describe in detail liquid phase processes for the production of 1,2-propanediol form glycerol. Whilst each makes passing reference to the possibility of the production being carried out in the vapour phase, neither document describes how the process can be efficiently and commercially carried out in the vapour phase to obtain high conversion and selectivity.

Whilst the processes described above offer means for obtaining desirable products from glycerol, they suffer from various disadvantages and drawbacks in terms of conversion, rate and/or economics and it is therefore desirable to provide alternative, and preferably improved, processes.

It has now been discovered that glycerol can be efficiently converted to the desired products by means of a hydrogenation reaction carried out in the vapour phase.

Thus according to one aspect of the present invention there is provided a process for hydrogenation of glycerol in which a feed comprising glycerol is contacted with a stream of a hydrogen-containing gas and subjected to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 secs.

It is surprising that it has been possible to carry out the hydrogenation reaction in the vapour phase since it has generally been believed that this was not possible due to the high boiling point of the glycerol. The requirement to use high temperatures would be anticipated to cause the glycerol to coke leading to operating problems. The high operating temperatures would also be expected to adversely affect the catalyst.

However, it has now been found that using the conditions of a temperature of from about 160° C. to about 260° C., a pressure of from about 10 to about 30 bar, a hydrogen to glycerol ratio of from about 400:1 to about 600:1 and a residence time of from about 0.01 to about 2.5 secs enables the expected problems to be obviated. Carrying out the hydrogenation in the vapour phase offers various advantages over prior art liquid phase processes. In general, the residence time in the hydrogenation reactor is less. This is advantageous since short residence times lead to the formation of fewer by-products. The present invention also makes it possible to operate at lower pressures whilst maintaining high overall selectivities to the desired products.

Any suitable process is used for the hydrogenation reaction. In one arrangement, the glycerol is vaporised into a stream of hydrogen-containing gas in a vaporiser before being passed to a hydrogenation reactor. It will be understood that the vaporiser and the hydrogenation reactor may be separate or may be zones located in the same reactor. Where a vaporiser is present, the hydrogen rich vapour stream will generally be passed directly to the hydrogenation reactor.

The hydrogen-containing gas stream may be fed to the vaporiser where present or to the hydrogenation reactor at any suitable temperature.

The hydrogenation-containing gas may include minor amounts of one or more inert gases which may include nitrogen, carbon oxides, neon, argon and/or low molecular weight hydrocarbons such as methane, ethane, propane, n-butane and iso-butane. Ethanol and ethyl acetate may also be present.

The glycerol feed may be from any source. It may be pure glycerol or it may contain other components such as other organic compounds, water and/or impurities. For example, the glycerol feed may include one or more of water, alcohols such as methanol, ethanol, propanol, hydroxy propanone, butanols and the like and esters. Involatile components may also be present. Where such components are present, they may be removed from the reaction by means of a purge which is usually taken form the bottom of the vaporiser. The other components present will largely depend on the source of the glycerol. Since the process of the present invention may be carried out in the presence of such components there is no requirement to purify the glycerol prior to it being used as a feedstock. This offers significant advantages when the process of the present invention is to be coupled to plants in which glycerol is formed as a by-product. The process of the present invention will also be able to operate in the presence of a high salt and/or ash content.

Any suitable catalyst system may be used. In a preferred arrangement, the catalyst will be provided as a fixed bed located in the hydrogenation reactor. Any suitable catalyst may be used. In one arrangement, a reduced copper catalyst may be used. Examples include copper/alumina/manganese, copper chromite, copper silica, copper zinc alumina, copper zinc oxide, raney copper and the like. Reduced nickel or reduced cobalt containing catalysts may also be used. Precious metal catalysts such as those containing ruthenium, palladium, platinum, rhodium and/or iridium may be used. These may be supported on, for example, carbon, alumina and silica.

The process may be carried out at any suitable reaction conditions within the ranges of the present invention. Preferred temperatures are from about 200° C. to about 240° C. Temperatures of from about 205° C. to about 220° C. are particularly suitable. Pressures in the range of from about 17 bar to about 23 bar preferred with a pressure of 20 bar being particularly suitable. A residence time of from about 0.3 to about 1.5 secs may be used with a residence time of about 0.5 secs being particularly suitable.

The ratio of hydrogen to glycerol in the hydrogenation reactor feed is a function of temperature and the operating pressure. Preferred hydrogen to glycerol ratio is in the range of form about 450:1 to about 550:1. A ratio of about 500:1 is most preferred.

Surprisingly the process of the present invention offers excellent conversion. Conversions in excess of 95%, 98% and even in excess of 99% have been noted. However, in the event of incomplete conversion, separation of product from glycerol is readily achieved and unreacted glycerol may be recycled. By-products which may be formed, such as 1-hydroxy propanone, may be recycled for further reaction to the desired product.

Water will be produced in the reaction and at least a portion of the water produced may be recycled. Thus, other than at start up it is not generally necessary to add water to the glycerol to protect the catalyst which has been a feature of liquid phase reactions.

In a most preferred embodiment, the present invention relates to the selective hydrogenation of glycerol. In one arrangement, the invention selectively forms 1,2-propanediol and in an alternative arrangement the invention selectively forms propanols.

In general reaction temperatures of less than about 210° C. favour the formation of the 1,2-propanediol while those of about 210° C. and above favour the formation of propanols.

The present invention will now be described with reference to the following examples.

EXAMPLES 1 to 6

A 0.75" reactor was charged with 75 g (50 mls) of catalyst DRD 9289 A, a copper based catalyst from Davy Process Technology Ltd, and reduced by conventional means. A feed of glycerol and methanol was fed to a heated vessel with the hydrogen at the reaction pressure and complete vapourisation of the feed mixture. The resultant gaseous stream was then passed to the reactor and contacted with the catalyst. Products removed from the reactor were condensed at 10° C. and were analysed on a Hewlett Packard HP3560 GC equipped with a micro TCD detector. The conditions for the various examples are set out in Table 1 and the results are set out in Table 2.

TABLE 1

|  | Example No | | | | | |
|---|---|---|---|---|---|---|
|  | 1 | 2 | 3 | 4 | 5 | 6 |
| Inlet Temperature ° C. | 200 | 200 | 195 | 195 | 195 | 195 |
| Pressure, bar | 20 | 20 | 20 | 20 | 20 | 20 |
| Residence Time, s | 0.97 | 0.45 | 0.78 | 0.69 | 0.35 | 0.31 |
| Hydrogen:Glycerol ratio | 461 | 477 | 597 | 572 | 595 | 599 |
| LHSV · Hr$^{-1}$ | 0.287 | 0.625 | 0.303 | 0.356 | 0.676 | 0.755 |

TABLE 2

|  | Example | | | | | |
|---|---|---|---|---|---|---|
| Product Sel, Mol % | 1 | 2 | 3 | 4 | 5 | 6 |
| Ethanol | 0.77 | 0.28 | 1.04 | 0.81 | 0.37 | 0.25 |
| 2-Propanol | 1.59 | 0.59 | 1.87 | 1.45 | 0.67 | 0.47 |
| 1-Propanol | 1.35 | 0.54 | 1.37 | 1.08 | 0.53 | 0.38 |
| Hydroxypropanone | 1.41 | 1.53 | 1.09 | 1.19 | 1.11 | 1.11 |
| Ethylene Glycol | 1.05 | 1.15 | 0.65 | 1.00 | 1.28 | 1.24 |
| Propylene Glycol | 93.28 | 95.65 | 93.71 | 94.13 | 95.98 | 96.51 |
| Others | 0.55 | 0.26 | 0.27 | 0.34 | 0.06 | 0.05 |
| Conversion | 100 | 97.63 | 100 | 100 | 99.94 | 99.54 |

The invention claimed is:

1. A process for hydrogenation of glycerol in which a feed comprising glycerol is contacted with a stream of a hydrogen-containing gas and subjected to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 hr$^{-1}$.

2. A process according to claim 1 wherein the glycerol feed is vaporised into a stream of hydrogen-containing gas in a vaporiser before being passed to a hydrogenation reactor.

3. A process according to claim 1 or claim 2 wherein the catalyst is provided as a fixed bed located in the hydrogenation reactor.

4. A process according to any one of claims 1 to 3 wherein the catalyst is a reduced copper catalyst.

5. A process according to any one of claims 1 to 4 wherein the reaction temperature is from about 200° C. to about 240° C.

6. A process according to any one of claims 1 to 5 wherein the reaction temperature is from about 205° C. to about 220° C.

7. A process according to any one of claims 1 to 6 wherein the reaction pressure is from about 17 bar to about 23 bar.

8. A process according to any one of claims 1 to 7 wherein the reaction pressure is from about 20 bar.

9. A process according to any one of claims 1 to 8 wherein the residence time is from about 0.3 secs to about 1.5 secs.

10. A process according to any one of claims 1 to 8 wherein the residue time is about 0.5 secs.

11. A process according to any one of claims 1 to 10 wherein the hydrogen to glycerol ratio is from about 450:1 to about 550:1.

12. A process according to any one of claims 1 to 11 wherein the hydrogen to glycerol ratio is from about 500:1.

13. A process according to any one of claims 1 to 12 wherein the process is selective for the formation of 1,2-propanediol.

14. A process according to claim 13 wherein the temperature is less than about 210° C.

15. A process according to any one of claims 1 to 12 wherein the process is selective for the formation of propanols.

16. A process according to claim 15 wherein the temperature is about 210° C. or more.

* * * * *

UNITED STATES PATENT AND TRADEMARK OFFICE
CERTIFICATE OF CORRECTION

PATENT NO. : 7,355,083 B2  Page 1 of 2
APPLICATION NO. : 11/668884
DATED : April 8, 2008
INVENTOR(S) : Tuck et al.

It is certified that error appears in the above-identified patent and that said Letters Patent is hereby corrected as shown below:

Column 4, claim 1, line 67: "$hr^{-1}$" should read -- secs --.

Column 5, claim 3, line 5: "claim 1 or" should be deleted.

Column 5, claim 4, line 8: "any one of claims 1 to 3" should read -- claim 1 --.

Column 5, claim 5, line 10: "any one of claims 1 to 4" should read -- claim 1 --.

Column 5, claim 6, line 13: "any one of claims 1 to 5" should read -- claim 5 --.

Column 5, claim 7, line 16: "any one of claims 1 to 6" should read -- claim 1 --.

Column 5, claim 8, line 18: "any one of claims 1 to 7" should read -- claim 7 --.

Column 5, claim 8, line 19: "from" should be deleted.

Column 5, claim 9, line 20: "any one of claims 1 to 8" should read -- claim 1 --.

Column 6, claim 10, line 1: "any one of claims 1 to 8" should read -- claim 9 --.

Column 6, claim 11, line 3: "any one of claims 1 to 10" should read -- claim 1 --.

Column 6, claim 12, line 6: "any one of claims 1 to 11" should read -- claim 11 --.

Column 6, claim 12, line 7: "from" should be deleted.

Column 6, claim 13, line 9: "any one of claims 1 to 12" should read -- claim 1 --.

UNITED STATES PATENT AND TRADEMARK OFFICE
CERTIFICATE OF CORRECTION

| | |
|---|---|
| PATENT NO. | : 7,355,083 B2 |
| APPLICATION NO. | : 11/668884 |
| DATED | : April 8, 2008 |
| INVENTOR(S) | : Tuck et al. |

It is certified that error appears in the above-identified patent and that said Letters Patent is hereby corrected as shown below:

Column 6, claim 15, line 15: "any one of claims 1 to 12" should read -- claim 1 --.

Signed and Sealed this

Twenty-second Day of July, 2008

JON W. DUDAS
*Director of the United States Patent and Trademark Office*